United States Patent [19]

Dubroeucq et al.

[11] Patent Number: 4,711,890

[45] Date of Patent: Dec. 8, 1987

[54] PHARMACEUTICAL COMPOSITIONS CONTAINING AZANAPHTHALENE-CARBOXAMIDE DERIVATIVES, AZANAPHTHALENE-CARBOXAMIDE DERIVATIVES AND PROCESS FOR THEIR USE

[75] Inventors: Marie-Christine Dubroeucq, Enghien-les-Bains; Gerard R. Le Fur, Le Plessis-Robinson; Christian L. A. Renault, Taverny, all of France

[73] Assignee: Rhone-Poulenc Sante, Courbevoie, France

[21] Appl. No.: 564,322

[22] Filed: Dec. 22, 1983

[30] Foreign Application Priority Data

Dec. 24, 1982 [FR] France .................. 82 21758

[51] Int. Cl.$^4$ ............... A61K 31/47; C07D 215/22
[52] U.S. Cl. .................. 514/311; 514/314; 540/597; 540/600; 544/116; 544/128; 544/284; 544/283; 546/167; 546/169
[58] Field of Search .......... 544/284; 424/251; 546/169, 167; 514/314, 311

[56] References Cited

U.S. PATENT DOCUMENTS 4,499,094 2/1985 Dubroeucq et al. ........... 514/311

OTHER PUBLICATIONS

Roushdi, et al., "Chemical Abstracts", vol. 58, 1963, col. 13912e.
Pagani, et al., "Chemical Abstracts", vol. 82, 1975, col. 27089r.
DeWit, et al., "J. Org. Chem.", vol. 46, 1981, pp. 172-175.

Primary Examiner—Glennon H. Hollrah
Assistant Examiner—James H. Turnipseed
Attorney, Agent, or Firm—Stevens, Davis, Miller & Mosher

[57] ABSTRACT

Compounds of the formula:

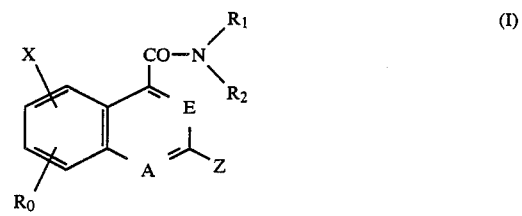

in which $R_1$ is $C_{1-6}$ alkyl, phenyl, $C_{3-6}$ cycloalkyl, phenylalkyl, cycloalkyl-alkyl or

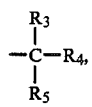

$R_3$ and $R_4$ being H or alkyl, $R_5$ being alkenyl or alkynyl, and the sum of the carbon atoms in $R_3$, $R_4$ and $R_5$ being 2 to 5, $R_2$ is as defined for $R_1$ and may also represent

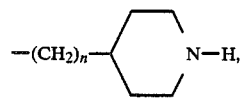

in which n is 0, 1, 2 or 3, it also being possible for $R_1$ and $R_2$ to form, with the nitrogen atom to which they are attached, a 5-, 6- or 7-membered heterocyclic radical which can contain another hetero-atom chosen from O and N and which can carry 1 or 2 substituents, Z is phenyl, pyridinyl, thienyl, thiazol-2-yl or substituted phenyl, X and $R_0$ are H, halogen, $C_{1-3}$ alkyl, $C_{1-3}$ alkoxy, nitro or $CF_3$, A represents N or CH and E represents N or CH, some of which are known compounds, are therapeutically useful compounds useful in the treatment of anxiety states or of pulmonary, renal, circulatory or cardiovascular disorders.

12 Claims, No Drawings

PHARMACEUTICAL COMPOSITIONS CONTAINING AZANAPHTHALENE-CARBOXAMIDE DERIVATIVES, AZANAPHTHALENE-CARBOXAMIDE DERIVATIVES AND PROCESS FOR THEIR USE

The present invention relates to pharmaceutical compositions containing naphthalene-carboxamide and azanaphthalenecarboxamide derivatives which can be used as medicaments for the treatment of anxiety states and of pulmonary, renal, cardiovascular or circulatory disorders, to certain new naphthalene-and azanaphthalene-carboxamide derivatives, and to processes for their preparation.

The present invention provides pharmaceutical compositions which comprise, as active ingredient, a compound of the general formula:

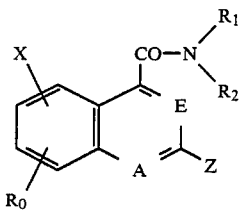

in which $R_1$ represents a linear or branched alkyl group having 1 to 6 carbon atoms, a phenyl group, a cycloalkyl group having 3 to 6 carbon atoms, a phenylalkyl group, the alkyl moiety of which contains 1 to 3 carbon atoms, a cycloalkyl-alkyl group, the cycloalkyl moiety of which contains 3 to 6 carbon atoms and the alkyl moiety of which contains 1 to 3 carbon atoms, or a

in which $R_3$ and $R_4$ are hydrogen atoms or alkyl groups and $R_5$ is an alkenyl or alkynyl group, the sum of the carbon atoms in $R_3$, $R_4$ and $R_5$ being 2 to 5, $R_2$ represents a linear or branched alkyl group having 1 to 6 carbon atoms, a phenyl group, a cycloalkyl group having 3 to 6 carbon atoms, a phenylalkyl group, the alkyl moiety of which contains 1 to 3 carbon atoms, a cycloalkyl-alkyl group, the cycloalkyl moiety of which contains 3 to 6 carbon atoms and the alkyl moiety of which contains 1 to 3 carbon atoms, a group

in which $R_3$, $R_4$ and $R_5$ are as defined above, or a

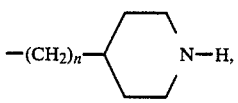

in which n is 0, 1, 2 or 3, it also being possible for $R_1$ and $R_2$ together to form, with the nitrogen atom to which they are attached, a 5-, 6- or 7-membered heterocyclic radical which may contain another heteroatom chosen from nitrogen and oxygen and which may carry one or two substituents chosen from amongst alkyl groups having 1 to 3 carbon atoms, the hydroxyl group, the oxo group and hydroxyalkyl, dimethylaminoalkyl and diethylaminoalkyl groups, the alkyl moieties of which contain 1 to 3 carbon atoms, Z represents a phenyl, pyridinyl, thienyl or thiazol-2-yl group or a phenyl group substituted by one or two substituents selected from amongst halogen atoms (e.g. chlorine, fluorine and bromine), alkyl, alkoxy and alkylthio groups having 1 to 3 carbon atoms, the trifluoromethyl group and the nitro group, X and $R_0$ are identical or different and represent hydrogen atoms or halogen atoms (e.g. fluorine, chlorine and bromine), alkyl or alkoxy groups having 1 to 3 carbon atoms or nitro or trifluoromethyl groups, A represents a nitrogen atom or a group CH and E represent a nitrogen atom or a group CH, or a mixture of stereoisomers thereof, or an acid addition salt thereof.

The following may be mentioned in particular as examples of heterocyclic radicals which can be formed by $R_1$ and $R_2$ with the nitrogen atom to which they are attached: pyrrolidinyl, piperidino, morpholino, piperazinyl, N-methylpiperazinyl, 1,2,3,6-tetrahydropyridyl, 2,3,4,5,6,7-hexahydroazepinyl, 4-oxopiperidino or piperidino substituted by one or two alkyl groups having 1 to 3 carbon atoms, by a hydroxyl group in the 3- or 4-position or by a hydroxyalkyl, dimethylaminoalkyl or diethylaminoalkyl group, the alkyl moiety of which has 1 to 3 carbon atoms.

In the formula (I) above, X and $R_0$ are preferably hydrogen atoms.

If the

contains one or more asymmetric carbon atoms, for given meanings of X, $R_0$, Z, A, E and

there are several stereoisomers corresponding to the planar formula (I). These various stereoisomers and also the corresponding racemates form part of the invention.

The compounds of formula (I) in which A is a nitrogen atom, E is a group CH, Z is a phenyl group, X and $R_0$ are both hydrogen atoms and $R_1$ and $R_2$ are identical alkyl groups containing 1 to 4 carbon atoms or form with the nitrogen atom to which they are attached a piperazino group are known compounds (cf British Patent 10 352; II Farmaco, vol. 29, 1974, 507–516, article by G. PAGANI et al; ROUSHDI et al, J. Pharm. Sci. U. Arab. Rep. 1961, 2, 109; WHITE et al., J. Org. Chem., 1942, 7, 497; SANNA, Chem. Zentr., 1941, 1, 1421). The compounds of formula (I) in which A and E are groups CH, Z is a phenyl or 3-chlorophenyl group, X is a hydrogen or chlorine atom or a trifluoromethyl group, $R_0$ is a hydrogen atom, and $R_1$ and $R_2$ are methyl groups are also known (cf. R. F. ABDULLA et al., J. Org. Chem.; 1980, 45, 1724–1725).

In addition, the compound of formula I in which A is a nitrogen atom, E is a group CH, Z is a 4-methylphenyl group, X and $R_0$ both represent hydrogen atoms, and $R_1$ and $R_2$ both represent ethyl groups is known (cf. JOHN et al., J. Prakt. Chem., 1931, 131, 301). Among the known compounds of formula (I) only a single compound, N,N-diethyl-2-phenylquinoline-4-carboxamide has been described as having pharmacological properties, more particularly uricosuric and anti-pyretic properties (GHAZAL et al., Egypt. Pharm. Bull., 1960, 42, 465).

The compounds of formula (I) other than those just mentioned are novel and constitute a feature of the present invention. Preferred compounds of formula (I) are those in which A and E are nitrogen atoms and X, $R_0$, Z, $R_1$ and $R_2$ are as hereinbefore defined, and those compounds in which A is a group CH, E is a nitrogen atom and X, $R_0$, Z, $R_1$ and $R_2$ are as hereinbefore defined. Also preferred are compounds of formula (I) in which A and E represent groups CH, $R_1$ is a linear or branched alkyl group having 2 to 6 carbon atoms, a phenyl group, a cycloalkyl group having 3 to 6 carbon atoms, a phenylalkyl group, the alkyl moiety of which contains 1 to 3 carbon atoms, a cycloalkyl-alkyl group, the cycloalkyl moiety of which contains 3 to 6 carbon atoms and the alkyl moiety of which contains 1 to 3 carbon atoms, a

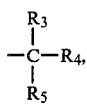

in which $R_3$, $R_4$ and $R_5$ are as hereinbefore defined, $R_2$ is a linear or branched alkyl group having 1 to 6 carbon atoms, a phenyl group, a cycloalkyl group having 3 to 6 carbon atoms, a phenylalkyl group, the alkyl moiety of which contains 1 to 3 carbon atoms, a cycloalkyl-alkyl group, the cycloalkyl moiety of which contains 3 to 6 carbon atoms and the alkyl moiety of which contains 1 to 3 carbon atoms, or a

in which $R_3$, $R_4$ and $R_5$ are as hereinbefore defined, or a

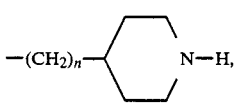

in which n is as hereinbefore defined, it also being possible for $R_1$ and $R_2$ together to form with the nitrogen atom to which they are attached, a 5-, 6- or 7-membered heterocyclic radical which may contain another heteroatom chosen from nitrogen and oxygen and which may carry one or two substituents chosen from amongst alkyl groups having 1 to 3 carbon atoms, the hydroxyl group, the oxo group, and hydroxyalkyl, dimethylaminoalkyl and diethylaminoalkyl groups, the alkyl moieties of which contain 1 to 3 carbon atoms, and Z, X and $R_0$ are as hereinbefore defined. Also preferred are the compounds of formula (I) in which A is a nitrogen atom, E is a group CH, Z, X and $R_0$ are as hereinbefore defined, $R_1$ and $R_2$ represent different alkyl groups, each containing from 1 to 6 carbon atoms, or $R_1$ is a phenyl group, a cycloalkyl group having 3 to 6 carbon atoms, a phenylalkyl group, the alkyl moiety of which contains 1 to 3 carbon atoms, a cycloalkyl-alkyl group, the cycloalkyl moiety of which contains 3 to 6 carbon atoms and the alkyl moiety of which contains 1 to 3 carbon atoms, or a

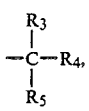

in which $R_3$, $R_4$ and $R_5$ are as hereinbefore defined, $R_2$ is a phenyl group, a cycloalkyl group having 3 to 6 carbon atoms, a phenylalkyl group, the alkyl moiety of which contains 1 to 3 carbon atoms, a cycloalkyl-alkyl group, the cycloalkyl moiety of which contains 3 to 6 carbon atoms and the alkyl moiety of which contains 1 to 3 carbon atoms, a

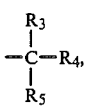

in which $R_3$, $R_4$ and $R_5$ are as hereinbefore defined, or a

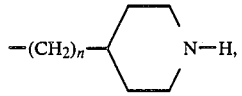

in which n is as hereinbefore defined, it also being possible for $R_1$ and $R_2$ together to form, with the nitrogen atom to which they are attached, a pyrrolidinyl, piperidino, morpholino, 1,2,3,6-tetrahydropyridyl, 2,3,4,5,6,7-hexahydroazepinyl, 4-oxopiperidino or piperidino group substituted by one or two alkyl groups having 1 to 3 carbon atoms, by a hydroxyl group in the 3- or 4-position or by a hydroxyalkyl, dimethylaminoalkyl or diethylaminoalkyl group, the alkyl moiety of which contains 1 to 3 carbon atoms.

According to a feature of the present invention the novel compounds of the general formula (I), are prepared by reacting an amine of the formula

(II)

in which $R_1$ and $R_2$ are as hereinbefore defined, with a compound of the formula:

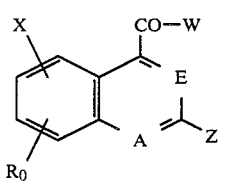
(III)

in which X, R₀, Z, A and E are as hereinbefore defined and W represents an alkoxy group of low molecular weight, preferably containing 1 to 4 carbon atoms, a chlorine atom or an alkoxycarbonyloxy group of low molecular weight, preferably containing 2 to 5 carbon atoms. The reaction proceeds in accordance with the equation:

(II)+(III)→(I)+WH          (1)

The reaction (1) may be carried out by known methods which make it possible to convert a carboxylic acid ester, a carboxylic acid chloride or a mixed anhydride to a carboxamide (cf e.g. C. A. BUEHLER and D. E. PEARSON, Survey of Organic Synthesis, Wiley Interscience, 1970, page 804). By the expression "known methods" is meant methods heretofore used or described in the chemical literature.

When W is an alkoxy group of low molecular weight, the reaction may be carried out, for example, by treating the ester of the formula (III) with at least an equimolecular amount of the amine of the formula (II), in the presence of a metallating agent such as butyllithium, and in an inert solvent such as diethyl ether or tetrahydrofuran, at a temperature of −70° C. to +30° C., or by heating the ester of the formula (III) in excess amine of the formula (II), at a temperature of 100° C. to 180° C., in the absence of a metallating agent.

When W is a chlorine atom, the reaction may be carried out, for example, by treating the acid chloride of the formula (III) with excess amine of the formula (II) in an inert solvent as toluene, chloroform or methylene chloride, at a temperature of between 20° C. and the boiling point of the solvent used. The excess amine of the formula (II) used, which acts as a base neutralising the hydrochloric acid formed in the reaction, is at least one equivalent, i.e. the total amount of amine of the formula (II) employed is at least two equivalents. In the case where at least one of the symbols A and E in the formula (III) represents a nitrogen atom, the acid chloride of the formula (III) can be used in the form of the hydrochloride provided that at least one additional equivalent of the amine of the formula (II) is employed so as to convert the acid chloride of the formula (III) from the hydrochloride form to the form of the free base.

When W is a chlorine atom, the reaction may also be carried out by reacting the acid chloride of the formula (III) with the amine of the formula (II) in the presence of a tertiary amine such as triethylamine, in an inert solvent such as those mentioned above, at a temperature of between 20° C. and the boiling point of the solvent. It is also possible to react the acid chloride of the formula (III) with the amine of the formula (II) in pyridine, which serves both as a base to take up the acid formed and as a solvent.

When W is an alkoxycarbonyloxy group of low molecular weight, the reaction may be carried out, for example, by treating the mixed anhydride of the formula (III) with the amine of the formula (II) in an inert solvent such as benzene, toluene, chloroform or methylene chloride, at a temperature of −5° C. to +25° C.

When the symbols R₁ and R₂ in the amine of formula (II) represent, with the nitrogen atom to which they are attached, a 5-, 6- or 7-membered heterocyclic ring substituted by an oxo group, the oxo group may, if appropriate, be protected by known methods during the reaction with the compound of general formula (III) with subsequent removal of the protecting group to yield the compound of formula (I). For example, when the amine of formula (II) is piperidin-4-one the oxo group in the 4-position may be protected in the form of a 1,4-ethylenedioxy group, using as starting material piperidin-4-one protected in the form of 1,4-dioxa-8-azaspiro[4,5]-decane.

The compounds of the formula (III) can be obtained by reacting a saturated aliphatic alcohol of low molecular weight, such as methanol or ethanol (when W is an alkoxy group of low molecular weight), a chlorinating agent such as thionyl chloride (when W is a chlorine atom) or an alkyl chloroformate of low molecular weight, such as methyl chloroformate or ethyl chloroformate (when W is an alkoxycarbonyloxy group of low molecular weight) with an acid of the formula:

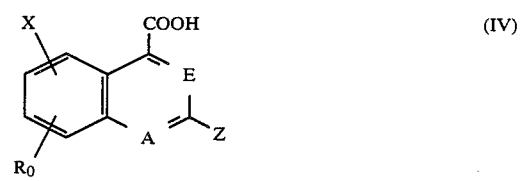

in which X, R₀, Z, A and E are as hereinbefore defined.

The reaction of the acid of the formula (IV) with the saturated aliphatic alcohol of low molecular weight can be carried out by heating the acid of the formula (IV) in the said alcohol at the reflux temperature, in the presence of a mineral acid such as sulphuric acid or hydrochloric acid.

The reaction of the acid of the formula (IV) with the chlorinating agent can be carried out in the absence of a solvent or in an inert solvent such as chloroform, preferably at the reflux temperature of the medium.

The reaction of the acid of the formula (IV) with the alkyl chloroformate of low molecular weight can be carried out in an inert solvent such as chloroform or methylene chloride, at a temperature of −5° C. to +25° C., in the presence of a tertiary amine such as triethylamine. The mixed anhydride formed in this way can then be reacted in situ, i.e. without prior isolation, with the amine of the formula (II).

According to a further feature of the present invention the novel compounds of the formula (I) in which R₂ is a

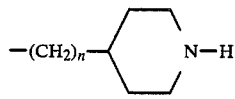

may also be prepared by reacting an amine of the formula:

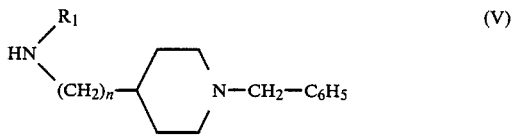

in which n and R₁ are as hereinbefore defined, with a compound of the formula (III) and then debenzylating the amide of the formula (VI) thus obtained. The reaction and debenzylation proceed according to the following reaction scheme:

(III) + (V) ⟶ (2)

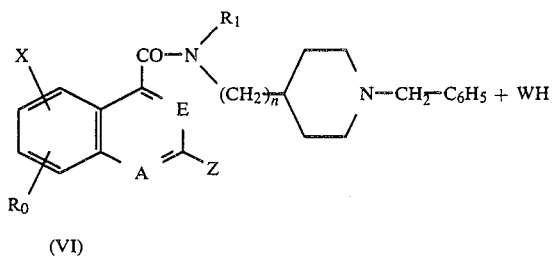

(VI)

(3) (VI) debenzylation (I) [in which

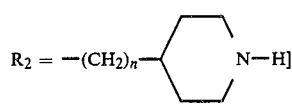

wherein the various symbols are as hereinbefore defined.

Reaction (2) is carried out under the same conditions as reaction (1). Reaction (3) (debenzylation) is carried out by known methods which make it possible to debenzylate tertiary N-benzylamines. The debenzylation may be carried out for example by reaction of hydrogen with the compound of the formula (VI) in the presence of a catalyst such as palladium (cf P. N. RYLANDER, Catalytic Hydrogenation over Platinum Metals, Academic Press, 1967, page 449), or by reaction of 2,2,2-trichloroethyl chloroformate with the compound of the formula (VI) (c.f. M. G. REINECKE et al., J. Org. Chem., 1973, 38, 3281).

A large number of carboxylic acids corresponding to the formula (IV) are known. Those which are unknown may be prepared by known methods, for example, by applying the methods previously used for the synthesis of the known acids of the formula (IV) to the appropriate starting materials (c.f. e.g. the documents mentioned below in Examples 2, 6, 7, 9, 10, 12 to 14, 20, 24, 35 and 54).

The reaction mixtures obtained by the various processes described above are treated by conventional physical methods (for example evaporation, solvent extraction, distillation, crystallisation or chromatography) or conventional chemical methods (e.g. salt formation and regeneration of the base) in order to isolate the compounds of the formula (I) in the pure state.

The compounds of the formula (I) in the form of the free base can, if appropriate, be converted by known methods into addition salts with an inorganic or organic acid by reaction with the acid in a suitable solvent.

For medicinal use, the compounds of general formula I can be employed as such or, optionally, in the form of pharmaceutically-acceptable acid addition salts, i.e. salts which are non-toxic at the use doses. Examples of pharmaceutically-acceptable acid addition salts are salts with inorganic acids (such as the hydrochlorides, sulphates, nitrates and phosphates) or with organic acids (such as the acetates, propionates, succinates, benzoates, fumarates, maleates, methanesulphonates, isethionates, theophyllineacetates, salicylates, phenolphthalinates and methylene-bis-$\beta$-hydroxynaphthoates) or substituted derivatives thereof.

The various clinical effects (anxiolytic, anticonvulsive, hypnotic and myorelaxant effects) of benzodiazepines have been attributed to the presence, in the central nervous system of mammals, of saturatable binding sites with a high affinity and "stereospecificity" (C. BRAESTRUP et al., Nature, 1977, 269, 702; J. F. TALLMAN et al., Science, 1980, 207, 274).

Some benzodiazepines also bind to membranes of peripheral tissues, such as the kidneys, also with a strong affinity (C. BRAESTRUP et al., Proc. Natl. Acad. Sci. USA, 1977, 74, 3805). The benzodiazepine receptors present in these tissues differ from those which may be labelled by [$^3$H] diazepam or [$^3$H] flunitrazepam in the brain. By way of example, clonazepam, which has a very strong affinity for the binding sites for [$^3$H] diazepam in the brain, is virtually inactive with respect to the binding sites for [$^3$H] diazepam in the kidneys. Conversely, one chlorine derivative of diazepam, Ro-5-4864, is very active at the peripheral level but inactive at the central level. Thus, it is possible to distinguish between at least two types of benzodiazepine receptors, one being of the "cerebral" type, the pharmacological criterion for which will be a classification by affinity decreasing in the order clonazepam > diazepam > Ro-5-4864, and the other being of the "peripheral" type, the pharmacological criterion for which will be a classification by affinity decreasing in the order Ro-5-4864 > diazepam > clonazepam.

These receptors of the "peripheral" type are present in numerous organs: the heart, the kidneys, the lungs, the blood platelets and also the brain (where both types of receptors are therefore present) (cf L. P. DAVIES et al., Eur. J. Pharmacol., 1981, 73, 209; J. K. T. WANG et al., Life Sciences, 1980, 27, 1881; J. W. REGAN et al., Life Sciences, 1981, 28, 991; H. SCHOEMAKER, Eur. J. Pharmacol., 1981 71, 173).

Although the compounds of general formula I have a different structure from the benzodiazepines, they have the property of binding to benzodiazepine receptors. Depending on their structure, they bind preferentially to cerebral receptors or peripheral receptors. By way of example, the compounds of the formula (I) in which X and $R_0$ are hydrogen atoms, A is a nitrogen atom, E is a nitrogen atom or a group CH, Z is the phenyl

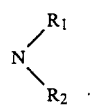

is a diethylamino, piperidino or pyrrolidino group act preferentially on cerebral receptors, whereas N,N-diethyl-3-phenylnaphthalene-1-carboxamide and the compounds of the formula (I) in which X and $R_0$ are hydrogen atoms, Z is a phenyl or 2-chlorophenyl or 3-chlorophenyl group and at least one of the substituents $R_1$ and $R_2$ is an alkyl group having 3 to 6 carbon atoms, which is branched in the $\alpha$-position to the nitrogen atom, and A and E are as hereinbefore defined, act preferentially on peripheral receptors.

The compound Ro-5-4864 referred to in the foregoing description is 7-chloro-5-(p-chlorophenyl)-1,3-dihydro-1-methyl-2H-1,4-benzodiazepin-2-one.

Compounds of formula (I) which are particularly preferred are those prepared in the following Examples 1, 4, 27, 15, 17 and 20. The compound of Example 1 is a known compound.

The Examples which follow illustrate the invention

EXAMPLE 1

N,N-diethyl-2-phenylquinoline-4-carboxamide

2-Phenylquinoline-4-carboxylic acid (30 g) is heated to the boil in thionyl chloride (100 ml). After heating under reflux for one hour, the thionyl chloride is evaporated off and the residue is taken up in toluene (100 ml), which is also evaporated off.

Toluene (100 ml) is then added to the residue obtained, followed by the addition of diethylamine (70 ml), with stirring. The reaction mixture is heated under reflux for one hour and then poured into water (500 ml). The organic phase is decanted and the aqueous phase is extracted with ethyl acetate (3×150 ml). The organic phases are combined, dried over magnesium sulphate and evaporated under reduced pressure. After crystallisation of the resulting residue from diethyl ether and recrystallisation from isopropyl alcohol, N,N-diethyl-2-phenylquinoline-4-carboxamide (18 g), melting at 110° C., is obtained.

EXAMPLE 2

N,N-diethyl-2-(pyridin-2-yl)-quinoline-4-carboxamide

The procedure of Example 1 is followed using 2-(pyridin-2-yl)-quinoline-4-carboxylic acid (15 g), thionyl chloride (45 ml) and diethylamine (6 ml) as the starting materials.

After recrystallisation of the residue from isopropyl ether, N,N-diethyl-2-(pyridin-2-yl)-quinoline-4-carboxamide (14.5 g), melting at 100° C., is obtained.

The 2-(pyridin-2-yl)-quinoline-4-carboxylic acid can be prepared by the process described by RISALITI, Ric., Scient., 28 (1958), 561, 563.

EXAMPLE 3

1-[2-(pyridin-2-yl)-quinolin-4-yl]-carbonylpiperidine 2-(Pyridin-2-yl)-quinoline-4-carboxylic acid (3 g) and thionyl chloride (10 ml) are heated under reflux for one hour. The thionyl chloride is evaporated off, the residue is taken up in toluene (100 ml) and the toluene is also evaporated off. Toluene (20 ml) is then added to the residue obtained, followed by the dropwise addition of piperidine (3.5 ml), with stirring. The reaction mixture is stirred for two hours at ambient temperature. It is then poured into water (50 ml). The organic phase is decanted and the aqueous phase is extracted with ethyl acetate (3×100 ml). The organic phases are combined, washed with water (3×30 ml), dried over magnesium sulphate and evaporated under reduced pressure.

After recrystallisation of the resulting residue from ethyl acetate, 1-[2-(pyridin-2-yl)-quinolin-4-yl]-carbonylpiperidine (2.9 g), melting at 158° C., is obtained.

EXAMPLE 4

1-(2-phenylquinolin-4-yl)-carbonylpiperidine

The procedure of Example 3 is followed using 2-phenylquinoline-4-carboxylic acid (8 g), thionyl chloride (24 ml) and piperidine (8.16 g) as the starting materials.

After recrystallisation of the residue from isopropyl ether, 1-(2-phenylquinolin-4-yl)-carbonylpiperidine (8.7 g), melting at 104° C., is isolated.

EXAMPLE 5

4-(2-phenylquinolin-4-yl)-carbonylmorpholine

The procedure of Example 3 is followed using 2-phenylquinoline-4-carboxylic acid (8 g), thionyl chloride (24 ml) and morpholine (8.3 g) as the starting materials.

After recrystallisation from ethanol, 4-(2-phenylquinolin-4-yl)-carbonylmorpholine (8 g), melting at 124° C., is obtained.

EXAMPLE 6

N,N-diethyl-2-(4-chlorophenyl)-quinoline-4-carboxamide

The procedure of Example 3 is followed using 2-(4-chlorophenyl)-quinoline-4-carboxylic acid (5 g), thionyl chloride (15 ml) and diethylamine (18 ml) as the starting materials.

After recrystallisation of the residue from isopropyl ether, N,N-diethyl-2-(4-chlorophenyl)-quinoline-4-carboxamide (4.2 g), melting at 105° C., is isolated.

The 2-(4-chlorophenyl)-quinoline-4-carboxylic acid can be prepared by the process described by R. F. BROWN et al., J. Amer. Chem. Soc. 68, 2705 (1946).

EXAMPLE 7

N,N-diethyl-2-(4-methoxyphenyl)-quinoline-4-carboxamide.

The procedure of Example 3 is followed using 2-(4-methoxyphenyl)-quinoline-4-carboxylic acid (5 g), thionyl chloride (15 ml) and diethylamine (18.4 ml) as the starting materials.

After recrystallisation of the residue from isopropyl ether, N,N-diethyl-2-(4-methoxyphenyl)-quinoline-4-carboxamide (3.8 g), melting at 128° C., is isolated.

The 2-(4-methoxyphenyl)-quinoline-4-carboxylic acid can be prepared by the process described by CIUSA and LUZZATTO, Gazz. Chim. Ital., 44, 64 (1914).

EXAMPLE 8

N,N-diethyl-2-(2-chlorophenyl)-quinoline-4-carboxamide

The procedure of Example 3 is followed using 2-(2-(chlorophenyl)-quinoline-4-carboxylic acid (5 g), thionyl chloride (15 ml) and diethylamine (12.7 ml) as the starting materials.

After recrystallisation of the residue from isopropyl ether, N,N-diethyl-2-(2-chlorophenyl)-quinoline-4-carboxamide (3.2 g), melting at 130° C., is isolated.

The 2-(2-chlorophenyl)-quinoline-4-carboxylic acid can be prepared by the process described by R. F. BROWN et al., J. Amer. Chem. Soc. 68, 2705 (1946).

EXAMPLE 9

N,N-diethyl-2-(3-trifluoromethylphenyl)-quinoline-4-carboxamide

The procedure of Example 3 is followed using 2-(3-trifluoromethylphenyl)-quinoline-4-carboxylic acid (6 g), thionyl chloride (18 ml) and diethylamine (18.5 ml) as the starting materials.

After recrystallisation of the residue from isopropyl ether, N,N-diethyl-2-(3-trifluoromethylphenyl)-quinoline-4-carboxamide (5.2 g), melting at 100° C., is isolated.

The 2-(3-trifluoromethylphenyl)-quinoline-4-carboxylic acid can be prepared by the process described by SHARGIER and LALEZARI, J. Chem. Eng. Data, 8, 276 (1963).

EXAMPLE 10

N,N-diethyl-2-(4-fluorophenyl)-quinoline-4-carboxamide

The procedure of Example 3 is followed using 2-(4-fluorophenyl)-quinoline-4-carboxylic acid (5 g), thionyl chloride (15 ml) and diethylamine (19.2 ml) as the starting materials.

After chromatography of the residue on silica gel with an eluant consisting of a hexane/ethyl acetate mixture (70/30), and recrystallisation from isopropyl ether of the product separated off in this way, N,N-diethyl-2-(4-fluorophenyl)-quinoline-4-carboxamide (0.86 g), melting at 114° C., is isolated.

The 2-(4-fluorophenyl)-quinoline-4-carboxylic acid can be prepared by the process described by Bu Hoi et al., Rec. Trav. Chim., 68, 781 (1949).

EXAMPLE 11

1-(2-phenylquinolin-4-yl)-carbonylpyrrolidine

The procedure of Example 3 is followed using 2-phenylquinoline-4-carboxylic acid (10 g), thionyl chloride (30 ml) and pyrrolidine (10.3 ml) as the starting materials. After recrystallisation of the residue from isopropanol, 1-(2-phenylquinolin-4-yl)-carbonylpyrrolidine (5.6 g), melting at 128° C., is thus isolated.

EXAMPLE 12

N,N-diethyl-6,7-dimethoxy-2-phenylquinoline-4-carboxamide

The procedure of Example 3 is followed using 6,7-dimethoxy-2-phenyliquinoline-4-carboxylic acid (2.5 g), thionyl chloride (8 ml) and diethylamine (8.2 ml) as the starting materials.

This gives N,N-diethyl-6,7-dimethoxy-2-phenylquinoline-4-carboxamide (2.9 g) in the form of an oil, which is converted to its hydrochloride, in acetone, by the addition of a solution of hydrogen chloride in ether. After recrystallisation from acetone, the hydrochloride melts at 140° C.

The 6,7-dimethoxy-2-phenylquinoline-4-carboxylic acid can be prepared by the process described by BORSCHE and BARTENHEIMER, Ann., 548, 50 (1941).

EXAMPLE 13

N,N-diethyl-6-methyl-2-phenylquinoline-4-carboxamide

The procedure of Example 3 is followed using 6-methyl-2-phenylquinoline-4-carboxylic acid (3.2 g), thionyl chloride (15 ml) and diethylamine (12.5 ml) as the starting materials.

After recrystallisation of the residue from isopropyl ether, N,N-diethyl-6-methyl-2-phenylquinoline-4-carboxamide (3.1 g), melting at 120° C., is obtained.

The 6-methyl-2-phenylquinoline-4-carboxylic acid can be prepared by the process described by BUCHMANN and HOWTON, J. Amer. Chem. Soc., 68, 2718 (1946).

EXAMPLE 14

N,N-diethyl-8-nitro-2-phenylquinoline-4-carboxamide

The procedure of Example 3 is followed using 8-nitro-2-phenylquinoline-4-carboxylic acid (32 g), thionyl chloride (9 ml) and diethylamine (11.5 ml) as the starting materials.

After recrystallisation of the residue from a cyclohexane/ethyl acetate mixture (1/1), N,N-diethyl-8-nitro-2-phenylquinoline-4-carboxamide (2.45 g), melting at 138° C., is isolated.

The 8-nitro-2-phenylquinoline-4-carboxylic acid can be prepared by the process described by BUCHMANN et al., J. Amer. Chem. Soc., 69, 380 (1947).

EXAMPLE 15

N-methyl-N-(1-methylpropyl)-2-(2-chlorophenyl)-quinoline-4-carboxamide

The procedure of Example 3 is followed using 2-(2-chlorophenyl)-quinoline-4-carboxylic acid (5.7 g), thionyl chloride (15 ml) and N-methylbut-2-ylamine (15 ml) as the starting materials.

After recrystallisation of the residue from isopropyl ether, N-methyl-N-(1-methylpropyl)-2-(2-chlorophenyl)-quinoline-4-carboxamide (5 g), melting at 118° C., is obtained.

EXAMPLE 16

N,N-di-(1-methylpropyl)-2-(2-chlorophenyl)-quinoline-4-carboxamide

The procedure of Example 3 is followed using 2-(2-chlorophenyl)-quinoline-4-carboxylic acid (2.83 g), thionyl chloride (10 ml) and N-(1-methylpropyl)-but-2-ylamine (5.16 g) as the starting materials.

After a first chromatography of the residue on silica gel with a cyclohexane/ethyl acetate mixture (1/1) as the eluant, and then a second chromatography under pressure on silica gel with a cyclohexane/ethyl acetate mixture (7/3) as the eluant, N,N-di-(1-methylpropyl)-2-(2-chlorophenyl)-quinoline-4-carboxamide (1.8 g), melting at 120° C., is obtained.

EXAMPLE 17

N-ethyl-N-(1-methylpropyl)-2-(2-chlorophenyl)-quinoline-4-carboxamide

The procedure of Example 3 is followed using 2-(2-chlorophenyl)-quinoline-4-carboxylic acid (2.8 g), thionyl chloride (10 ml) and N-ethylbut-2-ylamine (4 g) as the starting materials.

After recrystallisation of the residue from isopropyl ether, N-ethyl-N-(1-methylpropyl)-2-(2-chlorophenyl)-quinoline-4-carboxamide (0.9 g), melting at 95° C., is obtained.

EXAMPLE 18

1-[2-(2-chlorophenyl)-quinolin-4-yl]-carbonylpiperidine

The procedure of Example 3 is followed using 2-(2-chlorophenyl)-quinoline-4-carboxylic acid (2.8 g), thionyl chloride (10 ml) and piperidine (3.4 g) as the starting materials.

After recrystallisation of the residue from ethyl acetate, 1-[2-(2-chlorophenyl)-quinolin-4-yl]-carbonylpiperidine (2.1 g), melting at 129° C., is isolated.

EXAMPLE 19

N,N-diethyl-2-(thiazolin-2-yl)-quinoline-4-carboxamide

The procedure of Example 3 is followed using 2-(thiazolin-2-yl)-quinoline-4-carboxylic acid (0.8 g), thionyl chloride (20 ml) and diethylamine (10 ml) as the starting materials.

After chromatography of the residue on silica gel using a chloroform/ethyl acetate mixture (9/1) as the eluant, N,N-diethyl-2-(thiazolin-2-yl)-quinoline-4-carboxamide (0.3 g), melting at 97° C., is isolated.

The 2-(thiazolin-2-yl)-quinoline-4-carboxylic acid is obtained by reacting isatine ($1.4 \times 10^{-2}$ mol) with 2-acetylthiazole ($1.3 \times 10^{-2}$ mol) in a medium consisting of a 6N aqueous solution of potassium hydroxide (30 ml) and ethanol (10 ml), at the reflux temperature. It melts at 250° C.

The 2-acetylthiazole can be obtained by the process described by ADAMSON et al., J. Chem. Soc., (1969), 2270–3.

EXAMPLE 20

N,N-diethyl-3-phenylnaphthalene-1-carboxamide

The procedure of Example 3 is followed using 3-phenylnaphthalene-1-carboxylic acid (5 g) in place of 2-(pyridin-2-yl)-quinoline-4-carboxylic acid (3 g), thionyl chloride (20 ml) in place of thionyl chloride (10 ml) and diethylamine (4.5 ml) in pyridine (25 ml) in place of piperidine (3.5 ml) in toluene (20 ml). After recrystallisation from hexane, N,N-diethyl-3-phenylnaphthalene-1-carboxamide (3.4 g), melting at 65° C., is obtained.

The 3-phenylnaphthalene-1-carboxylic acid can be prepared by the process described by F. G. BADDAR et al., J. Chem. Soc., 1959, 1009.

EXAMPLE 21

N-methyl-N-(1-methylpropyl)-3-phenylnaphthalene-1-carboxamide

The procedure of Example 20 is followed using 3-phenylnaphthalene-1-carboxylic acid (4.3 g), thionyl chloride (20 ml) and N-methylbut-2-ylamine (1.5 g) in pyridine (20 ml) as the starting materials. After recrystallisation from petroleum ether, N-methyl-N-(1-methylpropyl)-3-phenylnaphthalene-1-carboxamide (2.8 g), melting at 125° C., is obtained.

EXAMPLE 22

N,N-diethyl-2-(2-chlorophenyl)-quinazoline-4-carboxamide

The procedure of Example 3 is followed using 2-(2-chlorophenyl)-quinazoline-4-carboxylic acid (2.16 g) and thionyl chloride (10 ml), and then diethylamine (10 ml) in toluene (20 ml), as the starting materials. After recrystallisation from isopropyl ether, N,N-diethyl-2-(2-chlorophenyl)-quinazoline-4-carboxamide (2.2 g), melting at 124° C., is obtained.

The 2-(b 2-chlorophenyl)-quinazoline-4-carboxylic acid can be prepared as follows: a mixture of N-phenyl-2-chlorobenzamide (15 g) and thionyl chloride (11 ml) is heated at 90° C. for 1 hour 30 minutes. The excess thionyl chloride is removed by distillation under reduced pressure and ethyl cyanoformate (7 g) and tin tetrachloride (18.2 g) are added. The reaction medium is heated at 140° C. for 10 minutes, cooled and poured into a mixture of methylene chloride and water, and the organic phase is washed with water, dried over magnesium sulphate and evaporated to dryness under reduced pressure. By chromatography of the residue on silica gel with a cyclohexane/ethyl acetate mixture (9/1) as the eluant, a product (7 g) is isolated, which is treated at the boil with 5N sodium hydroxide (10 ml) and ethanol (30 ml). The ethanol is removed by distillation under reduced pressure and the residue is taken up in water and ether. By acidification of the aqueous phase, 2-(2-chlorophenyl)-quinazoline-4-carboxylic acid (2.3 g), melting at 171° C., is obtained.

EXAMPLE 23

1-(2-phenylquinolin-4-yl)-carbonylpiperazine

2-Phenylquinoline-4-carboxylic acid (30 g) in thionyl chloride (90 ml) is heated under reflux for four hours. The thionyl chloride is evaporated off, the residue is taken up in diethyl ether (100 ml) and the diethyl ether is also evaporated off. The residue is added in portions to a stirred solution of piperazine (51.6 g) in methylene chloride (250 ml). The mixture is stirred overnight at ambient temperature. The solution is then taken up in methylene chloride (500 ml) and water (400 ml). The organic phase is separated off and the aqueous phase is washed with methylene chloride ($3 \times 100$ ml). The organic phases are combined, washed with water (150 ml), dried over magnesium sulphate and evaporated under reduced pressure.

The residue is taken up in a 0.1N aqueous solution of acetic acid (200 ml). The insoluble material is filtered off and washed with the 0.1N aqueous solution of acetic acid ($3 \times 20$ ml). The filtrate and the wash solutions are combined, rendered alkaline by the addition of a concentrated solution of potassium hydroxide and extracted with methylene chloride ($3 \times 150$ ml). The organic phase is washed with water ($3 \times 60$ ml), dried over magnesium sulphate and evaporated under reduced pressure. The residue is chromatographed on silica gel using a 9/1 toluene/diethylamine mixture as the eluant.

The crude base thus obtained is dissolved in ethanol and then converted to its dihydrochloride by the addition of a solution of hydrogen chloride in ether. After recrystallisation from ethanol, 1-(2-phenylquinolin-4-yl)-carbonylpiperazine dihydrochloride (2.4 g), melting above 250° C., is obtained.

EXAMPLE 24

N,N-diethyl-2-(4-methylphenyl)-quinoline-4-carboxamide

A 1.6M solution of butyllithium in hexane (22.5 ml) is added, at ambient temperature and under a nitrogen atmosphere, to diethylamine (5.5 ml) in anhydrous tetrahydrofuran (50 ml). After stirring for 15 minutes, the mixture is cooled to 0° C. and ethyl 2-(4-methylphenyl)-quinoline-4-carboxylate (5.25 g) is then introduced slowly. The mixture is stirred for 2 hours at ambient temperature. Acetic acid is then added slowly, at ambient temperature and with stirring, until decolouration takes place and a yellow solution is obtained. Water (100 ml) is then added, the tetrahydrofuran is evaporated off under reduced pressure and the residue is extracted with ethyl acetate ($3 \times 100$ ml). The organic phase is washed with water, dried over magnesium sulphate and evaporated under reduced pressure. The residue is chromatographed on silica gel with a cyclohexane/ethyl acetate mixture (80/20) as the eluant. After recrystallisation from isopropyl ether of the crude product isolated in this way, N,N-diethyl-2-(4-methylphenyl)-quinoline-4-carboxamide (1.1 g), melting at 145° C., is obtained.

The ethyl 2-(4-methylphenyl)-quinoline-4-carboxylate can be prepared by reacting ethanol with 2-(4-methylphenyl)-quinoline-4-carboxylic acid in the presence of concentrated sulphuric acid. It melts at 52° C.

The 2-(4-methylphenyl)-quinoline-4-carboxylic acid can be prepared by the process described by C. PREVOST et al., Compt. Rend. Acad. Sci., 258, 954 (1964).

EXAMPLE 25

N,N-diethyl-2-phenylquinazoline-4-carboxamide

The procedure of Example 24 is followed using ethyl 2-phenylquinazoline-4-carboxylate (2.9 g), diethylamine (3 ml), a 1.6M solution of butyllithium in hexane (10 ml) and tetrahydrofuran (10 ml) as the starting materials. After recrystallisation from ethanol, N,N-diethyl-2-phenylquinazoline-4-carboxamide (2.2 g), melting at 127° C., is obtained.

The ethyl 2-phenylquinazoline-4-carboxylate can be prepared by the process of H. MEERWEIN et al., Chem. Ber., 1956, 89, 224, omitting the hydrolysis to the acid. It melts at 55°-56° C.

EXAMPLE 26

1-[(2-phenylquinazolin-4-yl)-carbonyl]-pyrrolidine

The procedure of Example 24 is followed using ehtyl 2-phenylquinazoline-4-carboxylate (3 g), pyrrolidine (3 ml), a 1.6M solution of butyllithium in hexane (15 ml) and tetrahydrofuran (25 ml) as the starting materials. After recrystallisation from ethanol, 1-[(2-phenylquinazolin-4-yl)-carbonyl]-pyrrolidine (2.1 g), melting at 153° C., is obtained.

EXAMPLE 27

1-[(2-phenylquinazolin-4-yl)-carbonyl]-piperidine

The procedure of Example 24 is followed using ethyl 2-phenylquinazoline-4-carboxylate (3.3 g), piperidine, (2.5 ml), a 1.6M solution of butyllithium in hexane (15 ml) and tetrahydrofuran (20 ml) as the starting materials. After recrystallisation from ethanol, 1-[(2-phenylquinazolin-4-yl)-carbonyl]-piperidine (2.6 g), melting at 160° C., is obtained.

EXAMPLE 28

4-[(2-phenylquinazolin-4-yl)-carbonyl]-morpholine

The procedure of Example 24 is followed using ethyl 2-phenylquinazoline-4-carboxylate (3.1 g), morpholine (2 ml), a 1.6M solution of butyllithium in hexane (15 ml) and tetrahydrofuran (20 ml) as the starting materials. After recrystallisation from ethanol, 4-[(2-phenylquinazolin-4-yl)-carbonyl]-morpholine (3 g), melting at 148° C., is obtained.

EXAMPLE 29

1-[(2-phenylquinazolin-4-yl)-carbonyl]-piperidin-4-ol

The procedure of Example 24 is followed using ethyl 2-phenylquinazoline-4-carboxylate (2 g), piperidin-4-ol (1.4 g), a 1.6M solution of butyllithium in hexane (18 ml) and tetrahydrofuran (30 ml) as the starting materials. After recrystallisation from a mixture of methanol and methylene chloride, 1-[(2-phenylquinazolin-4-yl)-carbonyl]-piperidin-4-ol (2.1 g), melting at 209° C., is obtained.

EXAMPLE 30

2,3,4,5,6,7-hexahydro-1-[(2-phenylquinazolin-4-yl)-carbonyl]-azepine

The procedure of Example 24 is followed using ethyl 2-phenylquinazoline-4-carboxylate (3 g), 2,3,4,5,6,7-hexahydroazepine (2.8 ml), a 1.6M solution of butyllithium in hexane (15 ml), and tetrahydrofuran (20 ml) as the starting materials. After recrystallisation from ethanol, 2,3,4,5,6,7-hexahydro-1-[(2-phenylquinazolin-4-yl)-carbonyl]-azepine (2 g), melting at 140° C., is obtained.

EXAMPLE 31

4-methyl-1-[(2-phenylquinazolin-4-yl)-carbonyl]-piperidine

The procedure of Example 24 is followed using ethyl 2-phenylquinazoline-4-carboxylate (3 g), 4-methylpiperidine (2.95 ml), a 1.6M solution of butyllithium in hexane (15 ml) and tetrahydrofuran (20 ml) as the starting materials. After recrystallisation from ethanol, 4-methyl-1-[(2-phenylquinazolin-4-yl)-carbonyl]-piperidine (1 g), melting at 138° C., is obtained.

EXAMPLE 32

3-methyl-1-[(2-phenylquinazolin-4-yl)-carbonyl]-piperidine

The procedure of Example 24 is followed using ethyl 2-phenylquinazoline-4-carboxylate (3 g), 3-methylpiperidine (3 ml), a 1.6M solution of butyllithium in hexane (15 ml) and tetrahydrofuran (20 ml) as the starting materials. After recrystallisation from isopropyl ether, 3-methyl-1-[(2-phenylquinazolin-4-yl)-carbonyl]-piperidine (1 g), melting at 116° C., is obtained.

EXAMPLE 33

2-methyl-1-[(2-phenylquinazolin-4-yl)-carbonyl]-piperidine

The procedure of Example 24 is followed using ethyl 2-phenylquinazoline-4-carboxylate (3 g), 2-methylpiperidine (3 ml), a 1.6M solution of butyllithium in hexane (15 ml) and tetrahydrofuran (20 ml) as the starting materials. After recrystallisation from ethanol, 2-methyl-1-[(2-phenylquinazolin-4-yl)-carbonyl]-piperidine (1.7 g), melting at 150° C., is obtained.

EXAMPLE 34

1-[(2-phenylquinazolin-4-yl)-carbonyl]-piperidine-3-methanol

The procedure of Example 24 is followed using ethyl 2-phenylquinazoline-4-carboxylate (3 g), piperidine-3-methanol (2.9 g), a 1.6M solution of butyllithium in hexane (31 ml) and tetrahydrofuran (20 ml) as the starting materials. After recrystallisation from ethyl acetate, 1-[(2-phenylquinazolin-4-yl)-carbonyl]-piperidine-3-methanol (1 g), melting at 142° C., is obtained.

EXAMPLE 35

N,N-diethyl-6-chloro-2-(4-chlorophenyl)-quinoline-4-carboxamide

A 1.6M solution of butyllithium in hexane (12.5 ml) is added, at ambient temperature and under a nitrogen atmosphere, to diethylamine (3 ml) in anhydrous tetrahydrofuran (15 ml). After stirring for 1 hour, the mixture is cooled to −65° C. and ethyl 6-chloro-2-(4-chlorophenyl)-quinoline-4-carboxylate (3.4 g) in tetrahydrofuran (15 ml) is then introduced slowly. The mixture is stirred for 2 hours 30 minutes at −65° C., glacial acetic acid (4 ml) is then introduced, the temperature of the medium is allowed to rise to −10° C., water (50 ml) is added and the medium is finally allowed to return to ambient temperature. The tetrahydrofuran is evaporated off and the insoluble material is extracted with ethyl acetate (3×50 ml). The organic phase is washed with water, dried over magnesium sulphate and evaporated under reduced pressure.

The residue obtained is chromatographed on silica gel with a cyclohexane/chloroform mixture (50/50) as the eluant. After recrystallisation from ethyl acetate of the crude product isolated in this way, N,N-diethyl-6-chloro-2-(4-chlorophenyl)-quinoline-4-carboxamide (1.1 g), melting at 173° C., is obtained.

The ethyl 6-chloro-2-(4-chlorophenyl)-quinoline-4-carboxylate can be prepared by reacting ethanol with 6-chloro-2-(4-chlorophenyl)-quinoline-4-carboxylic acid in the presence of concentrated sulphuric acid. It melts at 130° C.

The 6-chloro-2-(4-chlorophenyl)-quinoline-4-carboxylic acid can be synthesised by the process described by LUTZ et al., J. Amer. Chem. Soc., 68, 1813–14 (1946).

EXAMPLE 36

N,N-diethyl-2-(3-chlorophenyl)-quinoline-4-carboxamide

The procedure of Example 35 is followed using diethylamine (4.3 ml), a 1.6M solution of butyllithium in hexane (20 ml) and methyl 2-(3-chlorophenyl)-quinoline-4-carboxylate (3.2 g) as the starting materials. This gives N,N-diethyl-2-(3-chlorophenyl)-quinoline-4-carboxamide (3.4 g), which is converted to its hydrochloride by adding a solution of hydrogen chloride in diethyl ether to a solution of the product in acetone. After recrystallisation from an ethanol/diethyl ether mixture (2/1), this hydrochloride melts at 165° C.

The methyl 2-(3-chlorophenyl)-quinoline-4-carboxylate can be prepared by reacting methanol with 2-(3-chlorophenyl)-quinoline-4-carboxylic acid in the presence of concentrated sulphuric acid. It melts at 101° C.

The 2-(3-chlorophenyl)-quinoline-4-carboxylic acid can be prepared by the process described by R. F. BROWN et al., J. Amer. Chem. Soc., 68, 2705 (1946).

EXAMPLE 37

N,N-diethyl-2-(3,4-dichlorophenyl)-quinoline-4-carboxamide

The procedure of Example 35 is followed using diethylamine (5 ml), a 1.6M solution of butyllithium in hexane (23 ml) and ethyl 2-(3,4-dichlorophenyl)-quinoline-4-carboxylate (4 g) as the starting materials. After 3 recrystallisations of the residue from isopropanol, N,N-diethyl-2-(3,4-dichlorophenyl)-quinoline-4-carboxamide (2.5 g), melting at 170° C., is isolated.

The ethyl 2-(3,4-dichlorophenyl)-quinoline-4-carboxylate can be prepared by reacting ethanol with 2-(3,4-dichlorophenyl)-quinoline-4-carboxylic acid in the presence of concentrated sulphuric acid. It melts at 74° C.

The 2-(3,4-dichlorophenyl)-quinoline-4-carboxylic acid can be prepared by the process described by R. F. BROWN et al., J. Amer. Chem. Soc., 68, 2705 (1946).

EXAMPLE 38

N,N-diethyl-2-(2-fluorophenyl)-quinoline-4-carboxamide

The procedure of Example 35 is followed using diethylamine (27 ml), a 1.6M solution of butyllithium in hexane (12.5 ml) and ethyl 2-(2-fluorophenyl)-quinoline-4-carboxylate (2 g) as the starting materials. After recrystallisation of the residue from isopropyl ether, N,N-diethyl-2-(2-fluorophenyl)-quinoline-4-carboxamide (2 g), melting at 92° C., is isolated.

The ethyl 2-(2-fluorophenyl)-quinoline-4-carboxylate can be prepared by reacting ethanol with 2-(2-fluorophenyl)-quinoline-4-carboxylic acid in the presence of concentrated sulphuric acid. It melts at 86° C.

The 2-(2-fluorophenyl)-quinoline-4-carboxylic acid can be prepared by the process described by R. F. BROWN et al., J. Amer. Chem. Soc., 68, 2705 (1946).

EXAMPLE 39

1-{[2-(2-chlorophenyl)-quinolin-4-yl]-carbonyl}-2,6-dimethylpiperidine 2-(2-Chlorophenyl)-quinoline-4-carboxylic acid (5.7 g) and thionyl chloride (15 ml) are heated under reflux for 1 hour. The thionyl chloride is evaporated off, the residue is taken up in toluene (40 ml) and the toluene is also evaporated off. Toluene (50 ml) is then added to the residue obtained, followed by the dropwise introduction of 2,6-dimethylpiperidine (6.78 g), with stirring. The mixture is stirred for 1 hour at ambient temperature, the precipitate is filtered off and the filtrate is evaporated under reduced pressure. The residue is taken up in water (50 ml) and chloroform (50 ml). The organic phase is decanted and the aqueous phase is extracted with chloroform (50 ml). The organic phases are combined, dried over magnesium sulphate and evaporated under reduced pressure.

After recrystallisation of the resulting residue from ethyl acetate, 1-{[2-(2-chlorophenyl)-quinolin-4-yl]-carbonyl}-2,6-dimethylpiperidine (3.8 g), melting at 163° C., is obtained.

EXAMPLE 40

N,N-diisobutyl-2(2-chlorophenyl)-quinoline-4-carboxamide 2-(2-Chlorophenyl)-quinoline-4-carboxylic acid (2.8 g) is heated under reflux for 1 hour in thionyl chloride (10 ml). The thionyl chloride is evaporated off, the residue is taken up in toluene (40 ml) and the toluene is also evaporated off. Toluene (20 ml) is then added to the residue obtained and a solution of diisobutylamine (5.16 g) in toluene (20 ml) is introduced dropwise, with stirring. The mixture is stirred overnight at ambient temperature and evaporated under reduced pressure, and the residue is taken up in chloroform (50 ml) and water (100 ml). The organic phase is decanted, dried over magnesium sulphate and evaporated under reduced pressure.

The residue obtained is dissolved in ethyl acetate (100 ml) and the organic phase is extracted with a normal solution of acetic acid (100 ml), washed with water (4×100 ml), dried over magnesium sulphate and evaporated under reduced pressure. The residue obtained is taken up in acetone and, after the addition of a solution of hydrogen chloride in ether, N,N-diisobutyl-2-(2- chlorophenyl)-quinoline-4-carboxamide hydrochloride (1.5 g), melting at 124° C., is isolated.

EXAMPLE 41

N-methyl-N-phenyl-2-phenylquinoline-4-carboxamide

2-Phenylquinoline-4-carboxylic acid chloride hydrochloride (10.7 g) is added in portions over a period of 15 minutes, with stirring, to a solution of N-methylaniline (12.8 g) in methylene chloride (75 ml), cooled to 0° C. The mixture is stirred for 2 hours 30 minutes at 10° C. The solution obtained is washed with a 20% strength solution of acetic acid in water (120 ml). The acetic acid solution is extracted with methylene chloride (100 ml). The organic phases are combined, washed with water (3×100 ml), dried over magnesium sulphate and evaporated under reduced pressure.

After recrystallisation of the residue from acetonitrile, N-methyl-N-phenyl-2-phenylquinoline-4-carboxamide (9.1 g), melting at 141° C., is obtained.

EXAMPLE 42

N,N-dimethyl-2-phenylquinoline-4-carboxamide

2-Phenylquinoline-4-carboxylic acid chloride hydrochloride (10.7 g) is added in portions over a period of 1 hour to a stirred solution of N,N-dimethylamine (18.9 g) in methylene chloride (100 ml), cooled to 0° C. The mixture is stirred for 1 hour at 0° C. The solution is evaporated under reduced pressure. The residue is taken up in methylene chloride (100 ml). The organic phase is washed with water (3×100 ml), dried over magnesium sulphate and evaporated under reduced pressure.

After recrystallisation of the residue from acetonitrile, N,N-dimethyl-2-phenylquinoline-4-carboxamide (7.9 g), melting at 158° C., is isolated.

EXAMPLE 43

N-methyl-N-(1-methylpropyl)-2-phenylquinoline-4-carboxamide

The procedure of Example 42 is followed using 2-phenylquinoline-4-carboxylic acid chloride hydrochloride (10.7 g) and N-methylbut-2-ylamine (10.5 g) in methylene chloride (75 ml) as the starting materials.

After recrystallisation from acetonitrile, N-methyl-N-(1-methylpropyl)-2-phenylquinoline-4-carboxamide (10.1 g), melting at 146° C., is isolated.

EXAMPLE 44

2-phenyl-4-[(1,2,3,6-tetrahydropyrid-1-yl)-carbonyl]-quinoline

The procedure of Example 41 is followed but 1,2,3,6-tetrahydropyridine (10 g) in methylene chloride (75 ml), and 2-phenylquinoline-4-carboxylic acid chloride hydrochloride (10.7 g), are used as the starting materials.

The base obtained is dissolved in diethyl ether and then converted to its hydrochloride by the addition of a solution of hydrogen chloride in ethanol. After recrystallisation from ethanol, 2-phenyl-4-[(1,2,3,6-tetrahydropyrid-1-yl)-carbonyl]-quinoline (7 g) is isolated in the form of the hydrochloride, which melts to form a paste at between 130° and 140° C.

EXAMPLE 45

N-benzyl-N-methyl-2-phenylquinoline-4-carboxamide

The procedure of Example 41 is followed but benzylmethylamine (14.5 g) in methylene chloride (100 ml), and 2-phenylquinoline-4-carboxylic acid chloride hydrochloride (9.1 g), are used as the starting materials.

After recrystallisation from acetonitrile, N-benzyl-N-methyl-2-phenylquinoline-4-carboxamide (7 g), melting at 106°–110° C., is isolated.

EXAMPLE 46

N-cyclohexyl-N-methyl-2-phenylquinoline-4-carboxamide

The procedure of Example 41 is followed using 2-phenylquinoline-4-carboxylic acid chloride hydrochloride (9.1 g) and N-methylcyclohexylamine (13.5 g) in methylene chloride (100 ml) as the starting materials.

After recrystallisation from acetonitrile, N-cyclohexyl-N-methyl-2-phenylquinoline-4-carboxamide (9.3 g), melting at 168° C., is isolated.

EXAMPLE 47

N-ethyl-N-[(piperidin-4-yl)-methyl]-2-phenylquinoline-4-carboxamide

A solution of N-ethyl-(1-benzylpiperidin-4-yl)methylamine (7 g) in toluene (50 ml) is added slowly, at ambient temperature, to a stirred solution of 2-phenylquinoline-4-carboxylic acid chloride (9.1 g) and triethylamine (8.4 ml) in toluene (100 ml). The reaction mixture is stirred for 1 hour at ambient temperature. It is run into water (100 ml) and the toluene is evaporated off under reduced pressure. Ether (200 ml) is then added. The organic phase is decanted and the aqueous phase is extracted with ether (100 ml). The organic phases are combined, washed with water (2×50 ml) and then extracted with a 2N aqueous solution of hydrochloric acid (3×20 ml). The acid aqueous phase is washed with ether, brought to pH 10 by the addition of a concentrated solution of sodium hydroxide and extracted with ether (3×150 ml). The ether phase is washed with water (3×50 ml) and concentrated under reduced pressure. This gives N-ethyl-N-[(1-benzylpiperidin-4-yl)-methyl]-2-phenylquinoline-4-carboxamide (12 g).

Debenzylation is carried out in the following manner:

N-Ethyl-N-[(1-benzylpiperidin-4-yl)-methyl]-2-phenylquinoline-4-carboxamide (9.6 g) is heated in ethanol (200 ml) until it has dissolved. After cooling, this solution is treated with a 4.5N ethanolic solution of hydrogen chloride (9.2 ml), 10% strength palladium-on-charcoal (2.9 g) as a catalyst and, finally, sodium acetate (1.7 g). The mixture is hydrogenated at 60° C., with stirring, under a hydrogen pressure equal to normal pressure (1 bar), for 5 hours. After 5 hours (at which time the amount of hydrogen absorbed is 470 ml), the catalyst is removed by filtration, the ethanol is evaporated off by distillation under reduced pressure, the residue is taken up in water (200 ml) and the mixture is brought to pH 10 by the addition of a concentrated solution of sodium hydroxide and extracted with ether (3×100 ml). The organic phase is washed with water (3×50 ml), dried over magnesium sulphate and evaporated under reduced pressure. N-ethyl-N-[(piperidin-4-yl)methyl]-2-phenylquinoline-4-carboxamide (5 g) is isolated in this way; it is dissolved in acetone and converted to the monohydrochloride by the addition of a solution of hydrogen chloride in ether. This monohydrochloride melts at 219° C.

The N-ethyl-(1-benzylpiperidin-4-yl)-methylamine can be prepared by reducing N-ethyl-1-benzoylpiperidine-4-carboxamide ($3 \times 10^{-2}$ mol) with lithium aluminium hydride ($6 \times 10^{-2}$ mol) in tetrahydrofuran (100 ml).

The N-ethyl-1-benzoylpiperidine-4-carboxamide can be prepared by reacting thionyl chloride ($6.7 \times 10^{-2}$ mol) with 1-benzoylpiperidine-4-carboxylic acid ($4.5 \times 10^{-2}$ mol) in chloroform (100 ml) and reacting the acid chloride thus obtained with ethylamine (0.22 mol) in toluene (30 ml).

The 1-benzoylpiperidine-4-carboxylic acid can be prepared by reacting benzoyl chloride (0.85 mol) with piperidine-4-carboxylic acid (0.85 mol) in the presence of a 10% strength solution of potassium carbonate (3,300 ml). This product melts at 134° C.

EXAMPLE 48

N-ethyl-N-(piperidin-4-yl)-2-phenylquinoline-4-carboxamide

Triethylamine (16 ml) is added slowly to a stirred suspension of 2-phenylquinoline-4-carboxylic acid chloride (17.5 g) in toluene (250 ml), followed, over a period of 30 minutes, by the addition of a solution of N-ethyl-1-benzylpiperidin-4-ylamine (12.6 g) in toluene (50 ml). The mixture is stirred for 4 hours at ambient temperature.

The reaction medium is run into water (250 ml), the toluene is evaporated off by distillation in vacuo and diethyl ether (200 ml) is added. The organic phase is decanted and the aqueous phase is extracted with diethyl ether ($2 \times 200$ ml). The organic phases are combined, washed with water ($2 \times 50$ ml), dried over magnesium sulphate and concentrated by distillation under reduced pressure. The residue is chromatographed on silica gel using a toluene/diethylamine mixture (9/1) as the eluant. This gives N-ethyl-N-(1-benzylpiperidin-4-yl)-2-phenylquinoline-4-carboxamide (25 g).

Debenzylation is carried out in the following manner: 2,2,2-Trichloroethyl chloroformate (8 g) is added to a stirred solution of N-ethyl-N-(1-benzylpiperidin-4-yl)-2-phenylquinoline-4-carboxamide (17 g) in toluene (340 ml). The mixture is heated under reflux for 6 hours, a further amount of 2,2,2-trichloroethyl chloroformate (1.6 g) is added and the mixture is heated under reflux for 2 hours. The reaction mixture is run into water (300 ml), rendered alkaline with a 2N aqueous solution of sodium hydroxide and extracted with ethyl acetate ($3 \times 150$ ml). The organic phase is washed with water ($2 \times 50$ ml), dried over magnesium sulphate and concentrated under reduced pressure.

Ethanol (450 ml) and then a 6N aqueous solution of potassium hydroxide (200 ml) are added to the oil obtained. The mixture is stirred for a few minutes and then heated under reflux for 6 hours with stirring. After evaporation of the ethanol under reduced pressure, the reaction mixture is taken up in water (300 ml) and then in a 6N aqueous solution of hydrochloric acid (180 ml) and, finally, extracted with chloroform ($3 \times 200$ ml). The organic phase is washed with water ($2 \times 50$ ml), dried over magnesium sulphate and evaporated under reduced pressure. The residue is chromatographed on silica gel using a toluene/methanol/diethylamine mixture (9/1/1) as the eluant. N-Ethyl-N-(piperidin-4-yl)-2-phenylquinoline-4-carboxamide (3.3 g) is isolated in this way.

This compound is dissolved in ethanol and then converted to its monohydrochloride by the addition of a solution of hydrogen chloride in ether. The monohydrochloride melts above 250° C.

The N-ethyl-1-benzylpiperidin-4-ylamine can be prepared by reducing N-acetyl-1-benzylpiperidin-4-ylamine ($6.4 \times 10^{-2}$ mol) with lithium aluminium hydride (0.128 mol) in tetrahydrofuran (200 ml). The N-acetyl-1-benzylpiperidin-4-ylamine can be prepared by reacting acetyl chloride ($1.15 \times 10^{-1}$ mol) with 1-benzyl-piperidin-4-ylamine ($1.05 \times 10^{-1}$ mol) in chloroform (100 ml), in the presence of triethylamine ($1.05 \times 10^{-1}$ mol).

EXAMPLE 49

N-ethyl-N-[2-(piperidin-4-yl)-ethyl]-2-phenylquinoline-4-carboxamide

Triethylamine (6.7 ml) is added to a stirred suspension of 2-phenylquinoline-4-carboxylic acid chloride (8.3 g) in toluene (50 ml), followed, over a period of 30 minutes, by the addition of a solution of N-ethyl-(1-benzylpiperidin-4-yl)-ethylamine (6 g) in toluene (50 ml). The reaction mixture is stirred for 20 hours at ambient temperature. It is run into water (100 ml), the toluene is evaporated off by distillation under reduced pressure, the residue is taken up in diethyl ether (200 ml), and triethylamine (0.8 ml) is added. The organic phase is decanted and the aqueous phase is extracted with diethyl ether ($2 \times 100$ ml). The organic phases are combined, washed with water ($2 \times 30$ ml), dried over magnesium sulphate and evaporated under reduced pressure. The residue is chromatographed on silica gel using a cycyclohexane/diethylamine mixture (9/1) as the eluant. This gives N-ethyl-N-[2-(1-benzylpiperidin-4-yl)-ethyl]-2-phenylquinoline-4-carboxamide (9.7 g).

Debenzylation is carried out in the following manner: 2,2,2-Trichloroethyl chloroformate (2.6 g) is added to a stirred solution of N-ethyl-N-[2-(1-benzylpiperidin-4-yl)-ethyl]-2-phenylquinoline-4-carboxamide (5.8 g) in toluene (100 ml). The reaction mixture is heated under reflux for 1 hour. It is run into water (100 ml), rendered alkaline with a 2N aqueous solution of sodium hydroxide and extracted with ethyl acetate ($3 \times 100$ ml). The organic phase is washed with water ($2 \times 30$ ml), dried over magnesium sulphate and evaporated under reduced pressure.

Ethanol (150 ml) is added to the oil obtained, followed by the addition of a 6N aqueous solution of potassium hydroxide (64 ml), with stirring. The mixture is heated under reflux for 2 hours and then stirred at ambient temperature for 15 hours. Water (100 ml) is added to the reaction medium, the ethanol is evaporated off by distillation under reduced pressure, a further amount of water (100 ml) is added and the mixture is then extracted with diethyl ether ($3 \times 150$ ml) and finally with methylene chloride (150 ml). The organic phases are combined and extracted with an N aqueous solution of acetic acid ($4 \times 25$ ml). The acetic acid phase is brought to pH 10 by the addition of a 2N aqueous solution of sodium hydroxide and extracted again with methylene chloride ($3 \times 50$ ml). The organic phase is washed with water (30 ml), dried over magnesium sulphate and evaporated under reduced pressure. The residue is chromatographed on silica gel using a toluene/diethylamine mixture (9/1) as the eluant. N-ethyl-N-[2-(piperidin-4-yl)-ethyl]-2-phenylquinoline-4-carboxamide (2.2 g) is isolated in this way. This compound is converted to its monohydrochloride in ethanol. The monohydrochloride melts at 210° C.

The N-ethyl-(1-benzylpiperidin-4-yl)-ethylamine can be prepared by reducing N-ethyl-(1-benzoylpiperidin-4-yl)-acetamide ($2.9 \times 10^{-2}$ mol) with lithium aluminium hydride ($5.8 \times 10^{-2}$ mol) in tetrahydrofuran (100 ml).

The N-ethyl-(1-benzoylpiperidin-4-yl)-acetamide can be prepared by reacting thionyl chloride ($6 \times 10^{-2}$ mol) with (1-benzoylpiperidin-4-yl)-acetic acid ($4 \times 10^{-2}$ mol) in chloroform (100 ml) and reacting the acid chloride thus obtained with ethylamine (0.2 mol) in toluene (130 ml).

The (1-benzoylpiperidin-4-yl)-acetic acid can be prepared by reacting benzoyl chloride ($1.2 \times 10^{-1}$ mol) with potassium (piperidin-4-yl)-acetate ($10^{-1}$ mol) in water (100 ml) at 0° C. It melts at 137° C.

EXAMPLE 50

N-ethyl-N-[3-(piperidin-4-yl)-propyl]-2-phenylquinoline-4-carboxamide

The procedure of Example 48 is followed using 2-phenylquinoline-4-carboxylic acid chloride (32 g) in toluene (250 ml), triethylamine (12.3 ml) and N-ethyl(1-benzylpiperidin-4-yl)-propylamine (11.4 g) in toluene (50 ml), as the starting materials. This gives N-ethyl-N-[3-(1-benzylpiperidin-4-yl)-propyl]-2-phenylquinoline-4-carboxamide (21 g).

Debenzylation is carried out as in Example 48, using N-ethyl-N-[3-(1-benzylpiperidin-4-yl)-propyl]-2-phenylquinoline-4-carboxamide (21 g) in toluene (400 ml), 2,2,2-trichloroethyl chloroformate (9 g), and then a 6N aqueous solution of potassium hydroxide (245 ml) and ethanol (550 ml), as the starting materials. After chromatography of the residue on silica gel using a toluene/diethylamine mixture (9/1) as the eluant, N-ethyl-N-[3-(piperidin-4-yl)-propyl]-2-phenylquinoline-4-carboxamide (10 g) is isolated; this is converted to its methanesulphonate in ethanol by the addition of an ethanolic solution of methanesulphonic acid. The methanesulphonate melts at 164° C.

The N-ethyl-(1-benzylpiperidin-4-yl)-propylamine can be prepared by reducing N-ethyl-(1-benzoylpiperidin-4-yl)-propionamide ($3.4 \times 10^{-2}$ mol) with lithium aluminium hydride ($6.9 \times 10^{-2}$ mol) in tetrahydrofuran (200 ml).

The N-ethyl-(1-benzoylpiperidin-4-yl)-propionamide can be prepared by reacting thionyl chloride ($8.6 \times 10^{-2}$ mol) with (1-benzoylpiperidin-4-yl)-propionic acid in chloroform (150 ml) and reacting the acid chloride thus obtained with ethylamine (2.85 mol) in toluene (150 ml).

The N-benzoylpiperidine-4-propionic acid can be prepared by the process described by KOELSCH (J. Amer. Chem. Soc., 1943, 65, 2460).

EXAMPLE 51

N-methyl-N-(1-methylpropyl)-3-phenylisoquinoline-1-carboxamide

Triethylamine (1.1 g) is added to 3-phenylisoquinoline-1-carboxylic acid (2.4 g) in chloroform (100 ml). The mixture is cooled to 10° C. and ethyl chloroformate (1.21 g) is added. After stirring for 40 minutes, N-methylbut-2-ylamine (1.1 g) is added and the mixture is stirred for 4 hours at ambient temperature. The organic phase is washed with a saturated aqueous solution of sodium carbonate, dried over magnesium sulphate and evaporated to dryness under reduced pressure. The residue is chromatographed on silica gel with a cyclohexane/ethyl acetate mixture (7/3) as the eluant, and the product recovered is recrystallised from isopropyl ether. This gives N-methyl-N-(1-methylpropyl)-3-phenylisoquinoline-1-carboxamide (1.36 g), melting at 125° C. after recrystallisation from isopropyl ether.

The 3-phenylisoquinoline-1-carboxylic acid can be obtained from 1-methyl-3-phenylisoquinoline. Using N-bromosuccinimide, 1-dibromomethyl-3-phenylisoquinoline is formed first and this is then oxidised with silver nitrate, firstly in a neutral medium and then in a basic medium. The acid melts at 134° C.

EXAMPLE 52

1-[(2-phenylquinazolin-4-yl)-carbonyl]-piperidine-4-ethanol

Ethyl 2-phenylquinazoline-4-carboxylate (1.7 g) and piperidine-4-ethanol (8 g) are heated at 150° C. for 4 hours. After cooling, water is added and the mixture is extracted with ethyl acetate. The organic phase is dried over magnesium sulphate and evaporated to dryness under reduced pressure. The residue is chromatographed on silica gel with ethyl acetate as the eluant, and the product recovered is recrystallized from isopropyl ether. This gives 1-[(2-phenylquinazolin-4-yl)-carbonyl]-piperidine-4-ethanol (0.5 g), melting at 146° C.

EXAMPLE 53

1-[(2-phenylquinazolin-4-yl)-carbonyl]-piperidin-4-one

A 1.6M solution of butyllithium in hexane (37 ml) is added, under a nitrogen atmosphere and at 0° C., to 1,4-dioxa-8-azaspiro[4,5]decane (7.5 ml) in anhydrous tetrahydrofuran (30 ml). After 30 minutes, a solution of ethyl 2-phenylquinazoline-4-carboxylate (8 g) in anhydrous tetrahydrofuran (30 ml) is added. After 2 hours at ambient temperature, water is added and the mixture is extracted with methylene chloride. The organic phase is washed with water, dried over magnesium sulphate and evaporated to dryness under reduced pressure. The residue is taken up in acetone (100 ml) and concentrated hydrochloric acid (20 ml) and the mixture is stirred for 5 hours at ambient temperature.

The mixture is diluted with water, the aqueous phase is extracted with methylene chloride and the organic phase is washed with a normal solution of sodium hydroxide and then with water, dried over magnesium sulphate and evaporated to dryness under reduced pressure. This gives a product (1 g) which is chromatographed on silica gel with a toluene/diethylamine mixture (95/5) as the eluant. A product (4.5 g) is recovered, which is recrystallised from a cyclohexane/ethyl acetate mixture (1/1). This gives 1-[(2-phenylquinazolin-4-yl)-carbonyl]-piperidin-4-one (2.3 g), melting at 161° C.

EXAMPLE 54

N,N-diethyl-2-phenyl-8-trifluoromethylquinoline-4-carboxamide

The procedure of Example 4 is followed using 2-phenyl-8-trifluoromethylquinoline-4-carboxylic acid (10 g), thionyl chloride (30 ml) and diethylamine (16.2 ml) as the starting materials.

After chromatography on silica gel with a cyclohexane/ethyl acetate mixture (70/30) as the eluant, and recrystallisation from an isopropyl ether/petroleum ether mixture (8/3), N,N-diethyl-2-phenyl-8-trifluoromethylquinoline-4-carboxamide (9.2 g), melting at 114° C., is isolated.

The 2-phenyl-8-trifluoromethylquinoline-4-carboxylic acid can be prepared by the process described by D. W. BOYKIN et al., J. Med. Chem., 11 (2), 273-277 (1968).

The pharmacological properties of the compounds of formula (I) are illustrated by their affinity for the receptor sites for benzodiazepines, which may be measured as described hereinafter.

Affinity for the receptor sites for benzodiazepines

This affinity is measured by the ability of the products to displace tritiated diazepam ($^3$H-diazepam) from its binding site and is expressed by a value $K_i$, in micromol ($\mu$M), which is calculated by the formula:

$$K_i = \frac{IC_{50}}{1 + \frac{C}{K_D}}$$

in which C represents the concentration of $^3$H-diazepam used, $K_D$ is an affinity constant characteristic of diazepam and $IC_{50}$ is the concentration of product required to obtain 50% inhibition of the binding of the $^3$H-diazepam.

The affinity of the compounds of formula (I) for the cerebral receptor sites for benzodiazepines was determined, by the method of MOHLER et al, Life Sciences, 1977, 20, 2101, on rat brain membranes.

The affinity of the compounds of formula (I) for the peripheral-type receptor sites was determined, using the procedure of BRAESTRUP et al., Proc. Natl. Acad. Sci. U.S.A., 1977, 74, 3805, on rat kidney membranes.

By way of example, the following results were obtained:

| Product | $K_i(\mu M)$ |
|---|---|
| Affinity for the cerebral-type receptor sites | |
| Example 1 | 0.05 |
| Example 3 | 0.16 |
| Example 4 | 0.04 |
| Example 5 | 0.09 |
| Example 10 | 0.21 |
| Example 11 | 0.13 |
| Example 24 | 0.33 |
| Example 25 | 0.39 |
| Example 26 | 0.09 |
| Example 27 | 0.07 |
| Example 38 | 0.31 |
| Example 49 | 0.40 |
| Example 53 | 0.27 |
| Chlorodiazepoxide | 0.08 |
| Affinity for the peripheral-type receptor sites | |
| Example 8 | 0.117 |
| Example 10 | 0.160 |
| Example 15 | 0.031 |
| Example 16 | 0.072 |
| Example 17 | 0.009 |
| Example 18 | 0.360 |
| Example 20 | 0.002 |
| Example 21 | 0.058 |
| Example 22 | 0.270 |
| Example 37 | 0.117 |
| Example 39 | 0.054 |
| Example 43 | 0.100 |
| Example 51 | 0.045 |
| Diazepam | 0.043 |
| Ro-5-4864 | 0.004 |

The acute toxicities of the compounds of formula (I) were determined on male mice of the CD1 strain (Charles RIVER) by oral administration. The $LD_{50}$ values were calculated, after 3 days of observation, by the cumulative method of J. J. REED and H. MUENCH (Amer. J. Hyg., 1938, 27, 493).

The compounds behave as substances of relatively low toxicity to mice, since the $LD_{50}$ values of the compounds are between 200 and 1,000 mg/kg.

The compounds of formula I, and their salts with a pharmaceutically acceptable acid, can be used, in human therapy, as the active ingredient in medicaments for the treatment of anxiety states and pulmonary, renal, cardiovascular or circulatory disorders. These medicaments contain a pharmaceutically acceptable vehicle, in addition to the said active ingredient, and can be presented in any of the forms used in the field of medicaments, such as tablets, capsules, gelatin capsules, suppositories, ingestible or injectable solutions.

The present invention provides a pharmaceutical composition which comprises, as active ingredient, a compound of formula I or a mixture of stereoisomers thereof, or a pharmaceutically acceptable acid addition salt thereof in association with a pharmaceutically acceptable carrier or coating. The compositions according to the invention can be administered orally, parenterally or rectally.

Tablets, pills, powders (in particular, in gelatin capsules or in cachets) or granules can be used as solid compositions for oral administration. In these compositions, the active compound of formula (I) is mixed with one or more inert diluents such as starch, cellulose, sucrose, lactose or silica. These compositions can also comprise substances other than diluents, e.g. one or more lubricants such as magnesium stearate or talc, a colorant, a coating (coated tablets) or a lacquer.

Pharmaceutically acceptable elixirs, solutions, suspensions, emulsions and syrups, containing inert diluents such as water, ethanol, glycerol, vegetable oils or paraffin oil, can be used as liquid compositions for oral administration. These compositions can also comprise substances other than diluents, e.g. wetting agents sweeteners, thickeners, flavourings or stabilisers.

Sterile compositions for parenteral administration are preferably suspensions, emulsions or aqueous or nonaqueous solutions. Water, propylene glycol, a polyethylene glycol, vegetable oils, in particular olive oil, injectable organic esters, e.g. ethyl oleate, or other suitable organic liquids can be employed as the solvent or vehicle. These compositions can also contain adjuvants, in particular wetting agents, agents for creating isotonicity, emulsifiers, dispersants and stabilisers. Sterilisation can be carried out in several ways, e.g. by filtration under aseptic conditions, by incorporating sterilising agents into the composition, by irradiation or by heating. The compositions can also be prepared in the form of sterile solid compositions which can be dissolved in an injectable sterile medium at the time of use.

Compositions for rectal administration are suppositories or rectal capsules, which contain, in addition to the active compound, excipients such as cacao butter, semi-synthetic glycerides or polyethylene glycols.

In general, the physician will determine the posology which he considers to be most appropriate, taking into account the age, the weight and all other factors intrinsic to the patient to be treated.

The dosage depends on the desired effects and the method of administration used. By way of example, by oral administration, it can be between 10 and 500 mg of active substance per day, with unit doses ranging from 2 to 100 mg of active substance.

All of the compounds of formula (I) can be used for the treatment of anxiety states. Compounds of formula (I) in which Z represents a phenyl, 2- or 4-fluorophenyl, 4-methylphenyl, pyridinyl or thienyl group, A represents a nitrogen atom, E represents a nitrogen atom or a group CH, the

is N,N-diethyl, or $R_1$ is as hereinbefore defined for formula (I) and $R_2$ represents a

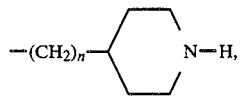

in which n is as hereinbefore defined, or $R_1$ and $R_2$ together with the nitrogen atom to which they are attached represent a 5-, 6- or 7-membered heterocyclic radical which may contain another heteroatom chosen from nitrogen and oxygen and which may carry one or two substituents selected from the hydroxyl group, the oxo group and hydroxyalkyl, dimethylaminoalkyl and diethylaminoalkyl groups, the alkyl moieties of which contain 1 to 3 carbon atoms, are useful only in the treatment of anxiety states: the remaining compounds of formula (I) can also be used for the treatment of anxiety states but are especially useful in the treatment of pulmonary, renal, circulatory or cardiovascular disorders (for example hypertension, epilepsy and angor).

We claim:

1. A pharmaceutical composition useful in the treatment of anxiety states or of pulmonary, renal, circulatory or cardiovascular disorders, which comprises as active ingredient, an effective amount of a compound of the formula:

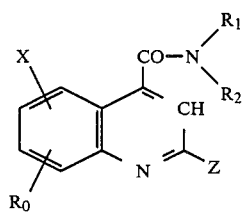

in which $R_1$ represents a linear or branched alkyl group having 1 to 6 carbon atoms, a phenyl group, a cycloalkyl group having 3 to 6 carbon atoms, a phenylalkyl group, the alkyl moiety of which has 1 to 3 carbon atoms, a cycloalkyl-alkyl group, the cycloalkyl moiety of which has 3 to 6 carbon atoms and the alkyl moiety of which has 1 to 3 carbon atoms, $R_2$ represents a linear or branched alkyl group having 1 to 6 carbon atoms, a phenyl group, a cycloalkyl group having 3 to 6 carbon atoms, a phenylalkyl group, the alkyl moiety of which has 1 to 3 carbon atoms, a cycloalkyl-alkyl group, the cycloalkyl moiety of which has 3 to 6 carbon atoms and the alkyl moiety of which has 1 to 3 carbon atoms or a

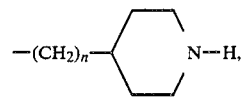

in which n is 0, 1, 2 or 3, or $R_1$ and $R_2$ together with the nitrogen atom to which they are attached represent a pyrrolidinyl, piperidino, 4-oxopiperidino or piperidino group substituted by one or two alkyl groups having 1 to 3 carbon atoms, by a hydroxyl group in the 3- or 4-position or by hydroxyalkyl, dimethylaminoalkyl or diethylaminoalkyl groups, the alkyl moiety of which has 1 to 3 carbon atoms, Z represents a phenyl, pyridinyl, thienyl or thiazol-2-yl group or a phenyl group substituted by one or two substituents selected from amongst halogen atoms, alkyl, alkoxy and alkylthio groups having 1 to 3 carbon atoms, the trifluoromethyl group and the nitro group, X and $R_0$ are identical or different and represent hydrogen atoms or halogen atoms, alkyl or alkoxy groups having 1 to 3 carbon atoms or nitro or trifluoromethyl groups, with the exception of a said compound in which Z represents a phenyl group, the

is N,N-diethyl and X and $R_0$ both represent hydrogen atoms, or a stereoisomer or mixture of stereoisomers thereof, or a pharmaceutically acceptable acid addition salt thereof, in association with a pharmaceutically acceptable carrier or coating.

2. A pharmaceutical composition according to claim 1 wherein, in the compound of formula (I), X and $R_0$ are hydrogen atoms.

3. A pharmaceutical composition according to claim 1 wherein, in the compound of formula (I), X and $R_0$ are hydrogen atoms, Z is the phenyl group and

is a piperidino or pyrrolidinyl group.

4. A pharmaceutical composition according to claim 1, wherein the active ingredient is a compound of formula (I), in which X and $R_0$ are hydrogen atoms, Z is a phenyl, 2-chlorophenyl or 3-chlorophenyl group and at least one of the substituents $R_1$ and $R_2$ is an alkyl group having 3 to 6 carbon atoms which is branched in the α-position to the nitrogen atom, or a pharmaceutically acceptable acid addition salt thereof.

5. A pharmaceutical composition according to claim 1, wherein the active ingredient is
1-(2-phenylquinolin-4-yl)-carbonylpiperidine,
N-methyl-N-(1-methylpropyl)-2-(2-chlorophenyl)-quinoline-4-carboxamide,
N-ethyl-N-(1-methylpropyl)-2-(2-chlorophenyl)-quinoline-4-carboxamide, or a pharmaceutically acceptable acid addition salt thereof.

6. A compound of formula (I):

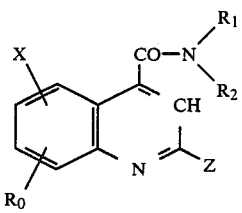 (I)

wherein Z represents a phenyl, pyridinyl, thienyl or thiazol-2-yl group or a phenyl group substituted by one or two substituents selected from amongst halogen atoms, alkyl, alkoxy and alkylthio groups having from 1 to 3 carbon atoms, the trifluoromethyl group and the nitro group, X and $R_0$ are identical or different and represent hydrogen atoms or halogen atoms, alkyl or alkoxy groups having from 1 to 3 carbon atoms or nitro or trifluoromethyl groups, with the exception of a said compound in which Z represents a phenyl group, the group

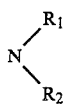

is N-N-diethyl and X and $R_0$ both represent hydrogen atoms; $R_1$ and $R_2$ represent different alkyl groups, each having from 1 to 6 carbon atoms, or $R_1$ is a phenyl group, a cycloalkyl group having from 3 to 6 carbon atoms, a phenylalkyl group, the alkyl moiety of which has from 1 to 3 carbon atoms, a cycloalkyl-alkyl group, the cycloalkyl moiety of which has from 3 to 6 carbon atoms and the alkyl moiety of which has from 1 to 3 carbon atoms, $R_2$ is a phenyl group, a cycloalkyl group having from 3 to 6 carbon atoms, a phenylalkyl group, the alkyl moiety of which has from 1 to 3 carbon atoms, a cycloalkyl-alkyl group, the cycloalkyl moiety of which has from 3 to 6 carbon atoms and the alkyl moiety of which has from 1 to 3 carbon atoms, or a

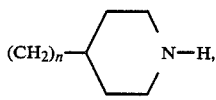

in which n is 0, 1, 2 or 3, or $R_1$ and $R_2$ together with the nitrogen atom to which they are attached represent a pyrrolidinyl, a piperidino, a 4-oxopiperidino or a piperidino group substituted by one or two alkyl groups having from 1 to 3 carbon atoms, by a hydroxy group in the 3- or 4- position or by a hydroxyalkyl, a dimethylaminoalkyl or a diethylaminoalkyl group, the alkyl moiety of which has from 1 to 3 carbon atoms; or a stereoisomer or mixture of stereoisomers thereof, or an acid addition salt thereof.

7. A compound according to claim 6 wherein X and $R_0$ represent hydrogen atoms.

8. A compound according to claim 6 which is 1-(2-phenylquinolin-4-yl)-carbonylpiperidine.

9. A compound according to claim 6 which is N-methyl-N-(1-methylpropyl)-2-(2-chlorophenyl)-quinoline-4-carboxamide.

10. A compound according to claim 6 which is N-ethyl N-(1-methylpropyl)-2-(2-chlorophenyl)-quinoline-4-carboxamide.

11. A method for the treatment of a patient suffering from, or subject to, an anxiety state, which comprises administering to the patient an amount of a compound of formula (I) wherein the various symbols are as defined in claim 1, or a stereoisomer or mixture of stereoisomers thereof, or a pharmaceutically acceptable acid addition salt thereof, sufficient to improve the condition of the patient.

12. A method for the treatment of a patient suffering from, or subject to, a cardiovascular disorder, which comprises administering to the patient an amount of a compound of formula (I) wherein the various symbols are as defined in claim 1 with the exception of a said compound in which Z represents a phenyl, 2- or 4-fluorophenyl, 4-methylphenyl, pyridinyl or thienyl group, the

is N,N-diethyl, or $R_1$ is as defined in claim 1 and $R_2$ represents a

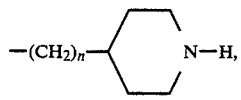

in which n is as hereinbefore defined, or $R_1$ and $R_2$ together with the nitrogen atom to which they are attached represent a pyrrolidinyl, piperidino, 4-oxopiperidino or piperidino group substituted by a hydroxyl group in the 3- or 4-position or by hydroxyalkyl, dimethylaminoalkyl or diethylaminoalkyl groups, the alkyl moiety of which has 1 to 3 carbon atoms, or a stereoisomer or mixture of stereoisomers thereof, or a pharmaceutically acceptable acid addition salt thereof, sufficient to improve the condition of the patient.

* * * * *